US00PP25834P2

(12) United States Plant Patent
Farrow

(10) Patent No.: US PP25,834 P2
(45) Date of Patent: Aug. 25, 2015

(54) ***ILEX* PLANT NAMED 'FARROWMRP'**

(50) Latin Name: *Ilex verticillata*
Varietal Denomination: FarrowMrP

(71) Applicant: Michael W. Farrow, Earleville, MD (US)

(72) Inventor: Michael W. Farrow, Earleville, MD (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 96 days.

(21) Appl. No.: 13/998,225

(22) Filed: Oct. 11, 2013

(51) Int. Cl.
*A01H 5/00* (2006.01)

(52) U.S. Cl.
USPC ..... Plt./247

(58) Field of Classification Search
USPC ..... Plt./247
CPC ..... A01H 5/00
See application file for complete search history.

*Primary Examiner* — Kent L Bell
(74) *Attorney, Agent, or Firm* — C. A. Whealy

(57) ABSTRACT

A new and distinct *Ilex* plant named 'FarrowMrP', characterized by its upright, low mounded and compact plant habit; freely branching habit; dense and bushy growth habit; flat dark green-colored leaves; typically only male flowers; and good garden performance.

2 Drawing Sheets

Botanical designation: *Ilex verticillata.*
Cultivar denomination: 'FarrowMrP'.

BACKGROUND OF THE INVENTION

The present Invention relates to a new and distinct *Ilex* plant, botanically known as *Ilex verticillata* and hereinafter referred to by the name 'FarrowMrP'.

The new *Ilex* plant originated from an open-pollination during the spring of 1999 of *Ilex verticillata* 'Red Sprite', not patented, as the female, or seed, parent with an unknown selection of *Ilex verticillata*, as the male, or pollen, parent. The new *Ilex* plant was discovered and selected by the Inventor during the summer of 2002 as a single plant within the progeny of the stated open-pollination in a controlled environment in Earleville, Md.

Asexual reproduction of the new *Ilex* plant by softwood cuttings in Earleville, Md. since the autumn of 2002 has shown that the unique features of the new *Ilex* plant are stable and reproduced true to type in successive generations of asexual reproduction.

SUMMARY OF THE INVENTION

Plants of the new *Ilex* have not been observed under all possible environmental conditions and cultural practices. The phenotype may vary somewhat with variations in environmental conditions such as temperature and light intensity without, however, any variance in genotype. The following traits have been repeatedly observed and are determined to be the unique characteristics of 'FarrowMrP'. These characteristics in combination distinguish 'FarrowMrP' as a new and distinct *Ilex* plant:

1. Upright, low mounded and compact plant habit.
2. Freely branching habit; dense and bushy growth habit.
3. Flat dark green-colored leaves.
4. Typically only male flowers observed.
5. Good garden performance.

Plants of the new *Ilex* differ from plants of the female parent, 'Red Sprite', in the following characteristics:

1. Plants of the new *Ilex* are more compact than plants of 'Red Sprite'.
2. Plants of the new *Ilex* typically only produces male flowers whereas plants of 'Red Sprite' typically only produces female flowers.

Plants of the new *Ilex* can be compared to the plants of *Ilex verticillata* 'Jim Dandy', not patented. In side-by-side comparisons conducted in Grand Haven, Mich., plants of the new *Ilex* differed from plants of 'Jim Dandy' in the following characteristics:

1. Plants of the new *Ilex* were more compact than plants of 'Jim Dandy'.
2. Plants of the new *Ilex* had darker green-colored leaves than plants of 'Jim Dandy'.

BRIEF DESCRIPTION OF THE PHOTOGRAPHS

The accompanying colored photographs illustrate the overall appearance of the new *Ilex* plant. The photographs show the colors as true as it is reasonably possible to obtain in colored reproductions of this type. Colors in the photographs may differ slightly from the color values cited in the detailed botanical description, which accurately describe the colors of the new *Ilex* plant.

The photograph on the first sheet is a side perspective view of a typical plant of 'FarrowMrP'.

The photograph on the second sheet is a close-up view of typical leaves, flower buds and flowers of 'FarrowMrP'.

DETAILED BOTANICAL DESCRIPTION

The aforementioned photographs and following observations and measurements describe plants grown during the spring, summer and autumn in ground beds in an outdoor nursery in Grand Haven, Mich. and under cultural practices typical of commercial production. Plants were four years old when the photographs and detailed description were taken. In the following description, color references are made to The Royal Horticultural Society Colour Chart, 1995 Edition, except where general terms of ordinary dictionary significance are used.

Botanical classification: *Ilex verticillata* 'FarrowMrP'.

Parentage:

*Female, or seed, parent.*—*Ilex verticillata* 'Red Sprite', not patented.

*Male, or pollen, parent.*—Unknown selection of *Ilex verticillata*, not patented.

Propagation:

*Type.*—By softwood cuttings.

*Time to initiate roots, winter.*—About 30 days at temperatures of 24° C.

*Time to produce a rooted young plant, summer.*—About four months at temperatures of 24° C.

*Root description.*—Fine, fibrous.

*Rooting habit.*—Freely branching; dense.

Plant description:

*Plant and growth habit.*—Perennial shrub; upright, low mounding and compact plant habit; moderately vigorous growth habit.

*Branching habit.*—Freely branching habit; dense and bushy growh habit with numerous lateral branches developing per plant.

*Plant height.*—About 30 cm.

*Plant diameter, area of spread.*—About 43 cm.

*Lateral branch description.*—Length: About 25 cm. Diameter: About 6 mm. Internode length: About 2 cm. Strength: Strong. Texture: Smooth, glabrous. Color, mature stems: Close to 197B.

*Leaf description.*—Arrangement: Alternate, simple. Length: About 6.5 cm. Width: About 4 cm. Shape: Obovate Apex: Acuminate. Base: Cuneate. Margin: Serrulate. Venation pattern: Pinnate. Texture, upper surface: Smooth, glabrous. Texture, lower surface: Pubescent. Aspect: Mostly flat. Color: Developing leaves, upper surface: Close to 143A. Developing leaves, lower surface: Close to 146B. Fully expanded leaves, upper surface: Close to 147A; venation, close to 143C. Fully expanded leaves, lower surface: Close to 147B; venation, close to 145B. Petioles: Length: About 1 cm. Diameter: About 2 mm. Texture, upper and lower surfaces: Smooth, glabrous. Color, upper and lower surfaces: Close to 145A.

Flower description:

*Flower appearance and arrangement.*—Single terminal and axillary rotate flowers; freely flowering habit with about 42 male flowers developing per lateral branch; flowers face mostly outwardly.

*Natural flowering season.*—Flowering commences in the middle of spring in Michigan; flowers last about three to four weeks on the plant; flowers not persistent.

*Fragrance.*—None detected.

*Flower diameter.*—About 3 mm.

*Flower length* (*height*).—About 4 mm to 5 mm.

*Flower buds.*—Length: About 2.5 mm to 3 mm. Diameter: About 3 mm. Shape: Obovate to globose. Color: Close to 154C.

*Petals.*—Quantity per flower: Five to six petals in a single whorl; fused at the base. Length: About 3 mm. Width: About 3 mm. Shape: Obovate. Apex: Obtuse. Margin: Entire. Texture, upper and lower surfaces: Smooth, glabrous. Color: When opening, upper and lower surfaces: Close to 155D. Fully opened, upper and lower surfaces: Close to 155D; color becoming closer to 157A with development.

*Calyx.*—Length: About 1 mm. Diameter: About 4 mm. Shape: Star-shaped. Sepal texture, upper and lower surfaces: Smooth, glabrous. Sepal color, upper and lower surfaces: Close to 145A.

*Peduncles.*—Length: About 1.5 mm. Diameter: Less than 1 mm. Strength: Strong. Aspect: Erect (if terminal) to about 45° from lateral branch axis. Texture: Smooth, glabrous. Color: Close to 144A.

*Reproductive organs.*—Androecium: Quantity of stamens per flower: About five. Anther length: About 1.5 mm. Anther shape: Oblong to globular. Anther color: Close to 145D. Pollen amount: Abundant. Pollen color: Close to 12B. Gynoecium: Female flowers have not been observed on plants of the new *Ilex*. Fruits and seeds: Fruit and seed development have not been observed on plants of the new *Ilex*.

Garden performance: Plants of the new *Ilex* have been observed to have good garden performance and to be tolerant to rain, wind and temperatures ranging from about −27° C. to about 38° C.

Pathogen & pest resistance: Plants have not been observed to be resistant to pathogens and pests common to *Ilex*.

It is claimed:

1. A new and distinct *Ilex* plant named 'FarrowMrP' as illustrated and described.

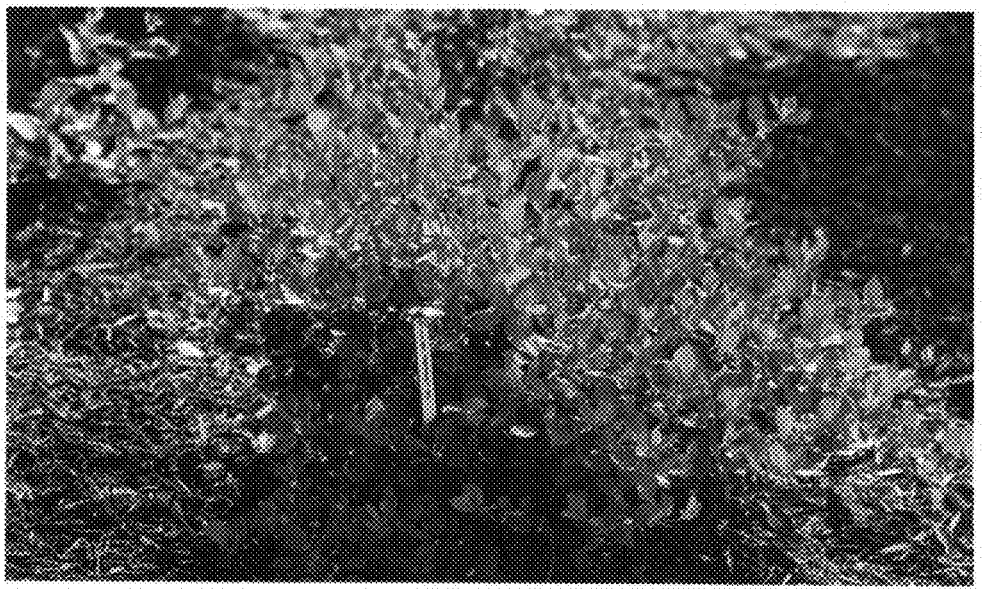

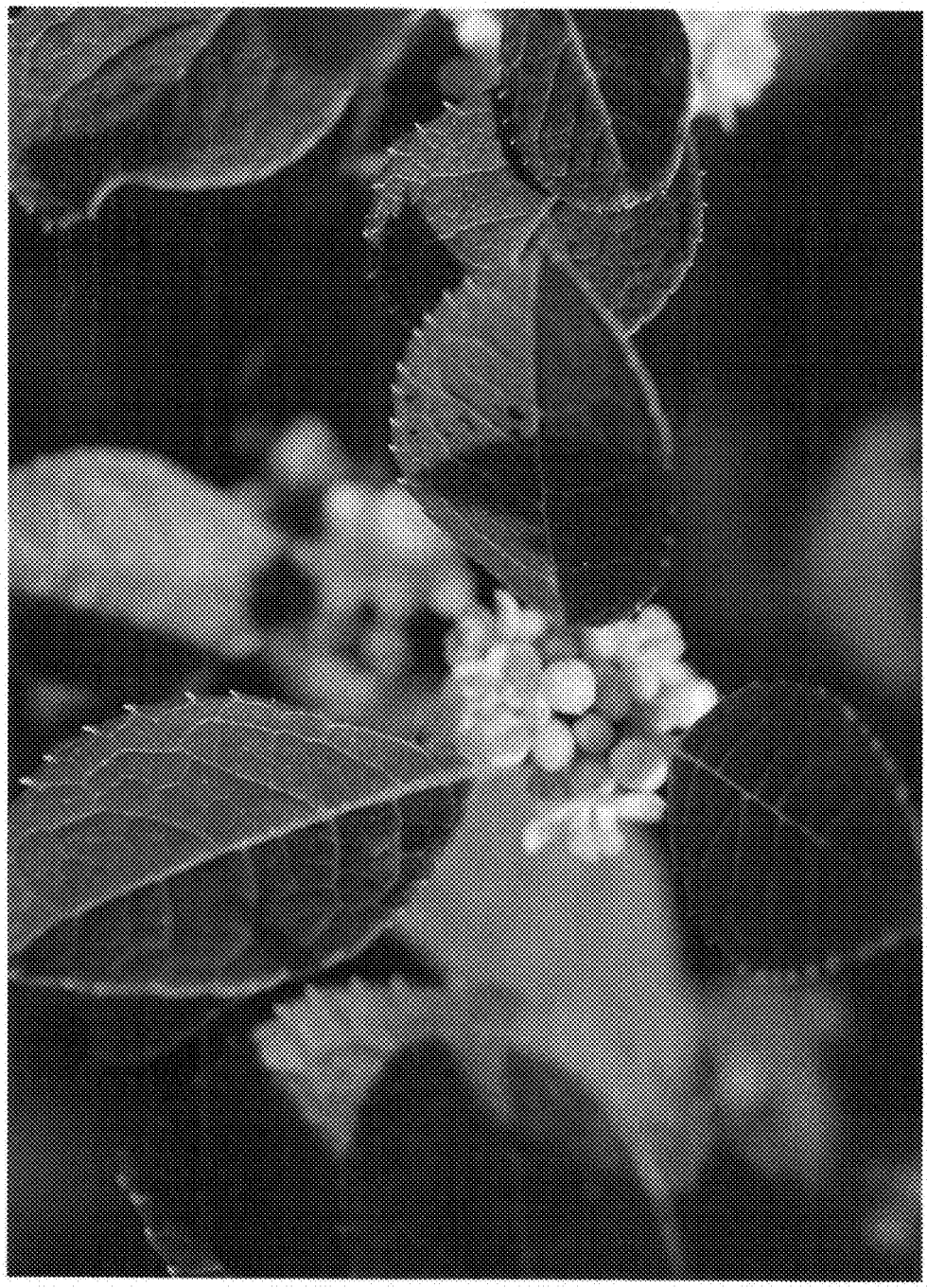

* * * * *